(12) United States Patent
Salmon et al.

(10) Patent No.: US 6,315,708 B1
(45) Date of Patent: Nov. 13, 2001

(54) STENT WITH SELF-EXPANDING END SECTIONS

(75) Inventors: Sean Salmon, Hollywood, FL (US); Dieter Stockel, Los Altos, CA (US); Robert E. Fischell, Dayton, MD (US); Tim A. Fischell, Richland, MI (US); David R. Fischell, Fair Haven, NJ (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/540,629

(22) Filed: Mar. 31, 2000

(51) Int. Cl.[7] ........................................... A61N 5/00
(52) U.S. Cl. ..................................................... 600/3
(58) Field of Search ................... 600/1, 2, 3, 4, 600/5, 6, 7, 8; 606/191, 194, 195; 604/96, 104; 623/1, 1.15, 12

(56) References Cited

U.S. PATENT DOCUMENTS

| | | | |
|---|---|---|---|
| 5,643,312 | 7/1997 | Fischell et al. | 606/198 |
| 5,695,516 | 12/1997 | Fischell et al. | 606/194 |
| 5,697,971 | 12/1997 | Fischell et al. | 623/1 |
| 5,913,895 | * 6/1999 | Burpee et al. | 623/1 |
| 5,968,069 | * 10/1999 | Dusbabek et al. | 606/194 |
| 6,206,911 | * 3/2001 | Milo | 623/1.15 |

* cited by examiner

Primary Examiner—John P. Lacyk
Assistant Examiner—Brian Szmal

(57) ABSTRACT

The present invention is a hybrid stent that is defined as having a central section that is balloon expandable and end sections that are self-expanding. The entire stent is mounted on a balloon of a balloon angioplasty catheter. One way to retain the self-expanding portion of the stent onto a balloon onto which it has been nested is to place a cylindrical elastomer tube around each of the self-expanding end sections of the stent. Another way to retain the hybrid stent onto a stent delivery system is to use a conventional sheath that is pulled back to initiate stent deployment

46 Claims, 2 Drawing Sheets

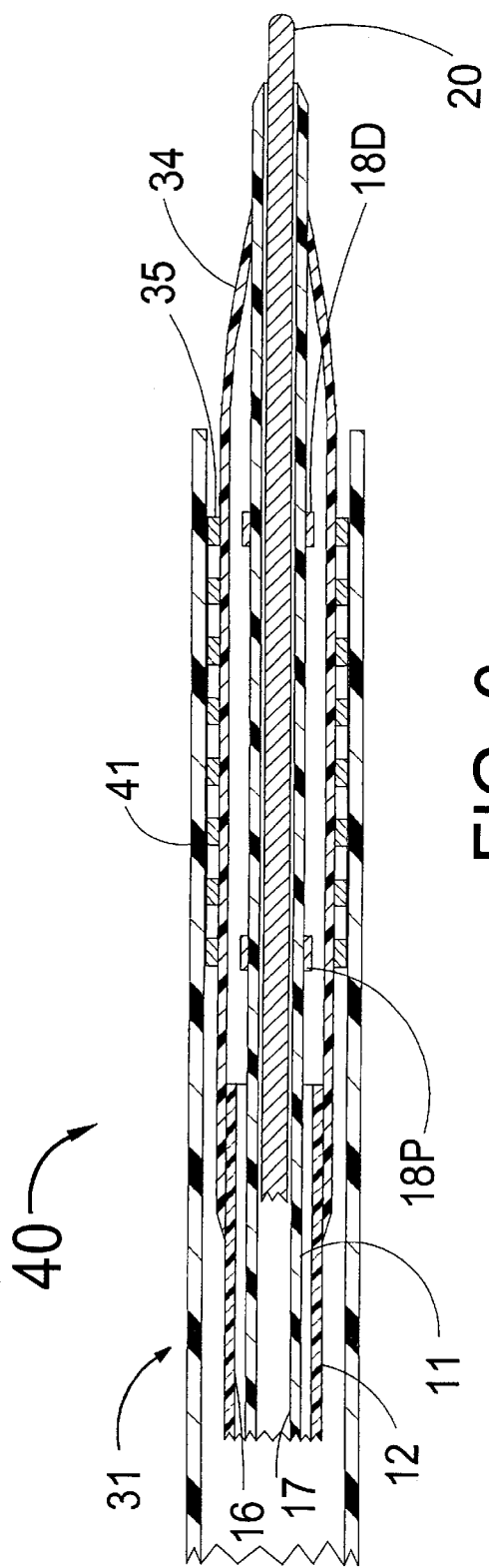
FIG. 3
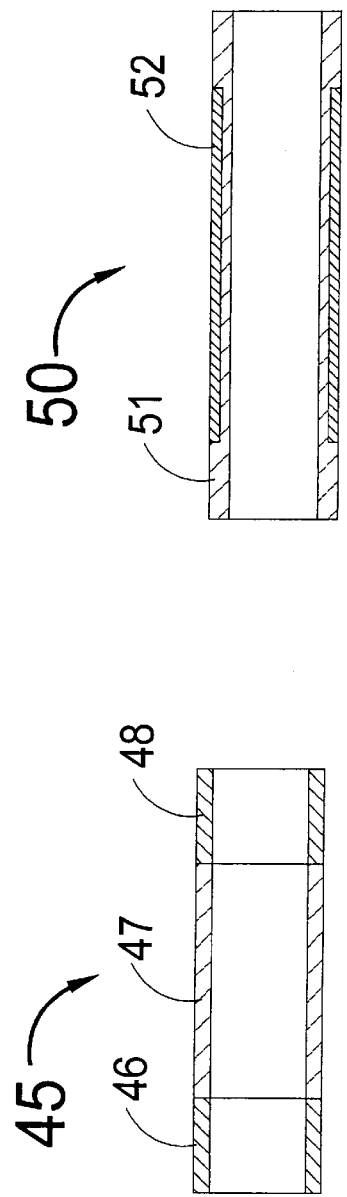
FIG. 4
FIG. 5

STENT WITH SELF-EXPANDING END SECTIONS

FIELD OF USE

This invention is in the field of medical devices to maintain the patency of vessels of the human body.

BACKGROUND OF THE INVENTION

Self-expanding stents, particularly those made from the shape-memory alloy Nitinol, are well known in the art of intravascular stents. These stents are typically placed within a sheath-like stent delivery system for placement into a stenosis of a vessel such as an artery of a human body. When the sheath of the stent delivery system is pulled back, the self-expanding stent will deploy radially outward against the wall of a vessel of a human body such as a coronary artery. After they are deployed, it is typically necessary to remove the sheath-like catheter that delivered the stent and then insert a balloon angioplasty catheter for the purpose of further expanding the stent at the site of an arterial stenosis. This results in additional time and cost for performing this procedure. The balloon that is used for further expansion of the stent is typically longer than the stent itself. Therefore, the regions of the artery just beyond the distal and proximal edges of the stent undergo some trauma caused by the expansion of the balloon. This trauma caused by the balloon expansion beyond the stent edges also occurs with balloon expandable stents.

One disadvantage of existing delivery systems for self-expanding stents (i.e., sheath-like catheters) is that they have a larger diameter as compared to a stent delivery system that does not use a sheath. Another disadvantage is that they have less flexibility and are therefore more difficult to deliver into highly curved arteries such as the coronary arteries. All stent delivery systems that have an expandable balloon extending beyond the edges of the stent can cause an "edge effect" which is a narrowing of the artery just beyond the edges of the stent. The edge effect is particularly pronounced when a radioisotope stent is placed into an arterial stenosis. Still another disadvantage of using a sheath to deploy a self-expanding stent is that it is more difficult to exactly position the stent within a stenosis as compared to the accurate positioning that is achievable with balloon expandable stents.

Because balloon expandable stents have the inflated balloon extending beyond the edges of the stent, arterial wall edge dissections are sometimes encountered. These dissections typically require an additional stent implantation to repair the dissection in order to decrease the possibility that acute or subacute thrombosis or restenosis will occur.

SUMMARY OF THE INVENTION

The goal of the present invention is to overcome several of the potential shortcomings of the existing stents and stent delivery systems. The present invention is a hybrid stent that is defined as having a central section that is balloon expandable and end sections that are self-expanding. The entire stent is mounted by nesting onto a balloon of a balloon angioplasty catheter, such as that described in U.S. patent application Ser. No. 09/444,105, incorporated herein by reference. An advantage of nesting is that the stent is retained on the balloon of the balloon angioplasty catheter, allowing more reliable insertion of a stent into tortuous vessels of a human body and a decreased probability of stent embolization.

A major difference between the present state of the art of stent nesting and the present invention is that existing nested stents are all of the balloon expandable type, but the present invention is a hybrid stent that is part balloon expandable and part self-expanding. One way to retain the self-expanding portion of the stent onto a balloon onto which it has been nested is to place a cylindrical elastomer tube around each of the self-expanding end sections of the stent. Another way to retain a hybrid stent onto a stent delivery system is to use a conventional sheath that is pulled back to initiate stent deployment.

An advantage of non-sheath embodiment of the present invention is that the stent can be delivered to a stenosis without a sheath-like stent delivery system. By using nesting and an elastomer tube over each end section of the stent, the need to employ a sheath can be eliminated. Thus, a more flexible and smaller outer diameter for the distal section of the stent delivery system can be produced. This allows for easier and more accurate placement of the stent as it is advanced through curved vessels of the human body and positioned within a stenosis. Therefore, the present invention is ideally suited for direct stenting, which precludes the need for pre-dilatation of an arterial stenosis.

Still another feature of the present invention is that the stent delivery system described herein uses a stent dilation balloon that has a cylindrical central section that is shorter in length as compared to the total length of the stent. Thus the end sections of stent are self-deployed against the vessel wall without the need for balloon expansion. However, the central portion of the stent is capable of being pushed under high pressure radially outward against the stenosis by inflating the balloon to a high pressure such as 16 atmospheres. The end sections of the stent are deployed by their own shape-memory characteristic outward into comparatively normal (i.e., non-stenosed) sections of an artery that are situated on either side of a stenosis. The lack of a high-pressure balloon deployment at the end sections of the stent reduces the trauma experienced by those sections of the artery into which the end sections are placed. Most importantly, having no inflated balloon extending beyond the edges of the stent will drastically reduce the incidence of arterial wall edge dissections. The high-pressure inflation of the balloon is used only to cause the balloon expandable central section of the stent to deploy radially outward against the typically high resistance of a stenosis. By this technique, the artery will not experience balloon trauma at the regions of the artery at and just beyond the edges of the stent. Thus the artery will have a decreased propensity for arterial wall dissections and edge stenoses. This is particularly important for a radioisotope stent that has an increased propensity to exhibit arterial narrowing just proximal and just distal to the edges of the radioisotope stent.

An object of the present invention is to have a hybrid stent that has a balloon expandable central section and self-expanding end sections.

Another object of the invention is to have a stent made from a shape-memory alloy that has a transition temperature for its central section that is distinctly higher than body temperature and a transition temperature for its end sections that is below normal body temperature.

Still another object of the invention is to have a stent that has a central section formed from a conventional metal such as stainless steel that is balloon expandable and also has end sections that are formed from a shape-memory metal having a transition temperature that is less than body temperature.

Still another object of the present invention is to obviate the need for a sheath when delivering a stent having self-expanding end sections into a vessel of a human body thereby providing a smaller outside diameter for the stent delivery system.

Still another object of this invention is to use a stent delivery system that has a distal section that includes the hybrid stent, which stent delivery system has greater longitudinal flexibility as compared to a sheathed stent.

Still another object of the invention is to use a hybrid stent in order to decrease the likelihood of balloon trauma to the vessel walls that are at and beyond the edges of the stent.

Still another object of the invention is to have a hybrid stent that has self-expanding end sections and an inflatable balloon that does not extend beyond the edges of the stent, the combination being capable of drastically reducing the incidence of arterial wall dissections resulting from stent implantation.

Still another object of the invention is to use a sheath as part of the stent delivery system for the hybrid stent.

Still another object of the invention is to have a more accurate means for placing a stent that has at least some portion that is self-expanding.

Still another object of the invention is to have a radio-isotope hybrid stent that has self-expanding end sections to reduce trauma to arterial walls situated near the proximal and distal edges of the stent.

Still another object of the invention is to have a stent delivery system including a stent that has self-expanding end sections that can be used for direct stenting of an arterial stenosis.

These and other objects and advantages of this invention will become apparent to a person of ordinary skill in this art upon reading the detailed description of this invention including the associated drawings as presented herein.

BRIEF DESCRIPTION OF THE DRAWINGS

FIG. 3 is a longitudinal cross section of a distal section of a system for deploying a hybrid stent that is crimped but not nested onto a non-inflated balloon; the stent delivery system utilizing a sheath to prevent premature deployment of the self-expanding end sections of the stent.

FIG. 4 is a longitudinal cross section of the present invention showing a balloon expandable stent center section joined to two self-expanding end sections.

FIG. 5 is a longitudinal cross section of a hybrid stent that has a self-expanding portion for all of the length of the stent and a longitudinally centered, balloon expandable section co-axially placed onto the self-expanding portion.

DETAILED DESCRIPTION OF THE INVENTION

Figure 1:
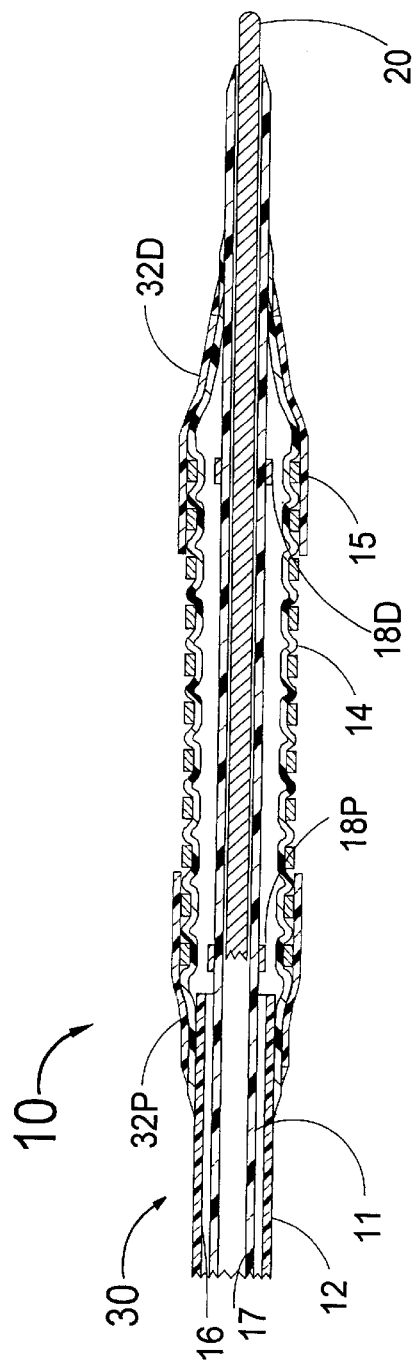
FIG. 1 is a longitudinal cross section of a distal section of a system comprising a guide wire and a balloon angioplasty catheter with a stent having self-expanding end sections; the stent being nested onto the catheter's non-inflated balloon.

FIG. 1 is a longitudinal cross section of a distal section of a system 10 that includes a hybrid stent 15, a guide wire 20, a balloon angioplasty catheter 30 and proximal and distal elastomer tubes 32P and 32D. The balloon angioplasty catheter 30 has an inner shaft 11, an outer shaft 12, an inflatable balloon 14, a balloon inflation lumen 16, a guide wire lumen 17, a proximal radio-opaque marker band 18P and a distal radio-opaque marker band 18D. As can be seen in FIG. 1, the balloon 14 has been formed into the interstices of the stent 15, which is a technique called "nesting". A method for nesting a stent onto a balloon of a balloon angioplasty catheter is described in detail in U.S. patent application Ser. No. 09/444,105,incorporated herein by reference.

The stent 15 would typically be fabricated from the metal "Nitinol" which is a shape- memory alloy that is well known in the art of vascular stents. The transition temperature of the metal of the end sections of the stent 15 would be set below 37 degrees Centigrade. For hybrid stents made entirely from a shape-memory alloy, the transition temperature for the central section of the stent 15 would be higher than 39 degrees Centigrade. The transition temperature is defined as the temperature at which the shape-memory metal stent assumes its preset state that, in air, is the state whereby the stent achieves its nominal deployed diameter. With a transition temperature for the end sections that is just below body temperature, the stent 15 would not tend to deploy at room temperature. However, the stent end sections will deploy when the stent 15 is placed into a human body and the balloon 14 is inflated which causes the tubes 32P and 32D to move longitudinally outward so as to uncover the self-expanding ends of the stent 15. Thus the stent 15 can be delivered to the site of a stenosis without requiring a sheath that has the undesirable effects of having a larger diameter and also being less flexible.

The proximal and distal elastomer tubes 32P and 32D would typically be made from an elastomer such as silicone rubber or polyurethane or a similar plastic material. The tubes 32P and 32D would each be solvent swelled and then placed in position as shown in FIG. 1. After the solvent evaporates out of the elastomer material, the tubes 32P and 32D will each contract around the end sections of the stent 15. In that position they are capable of preventing the expansion of the end sections of the stenosis 15 when the stent is introduced into a patient's vascular system.

Figure 2:
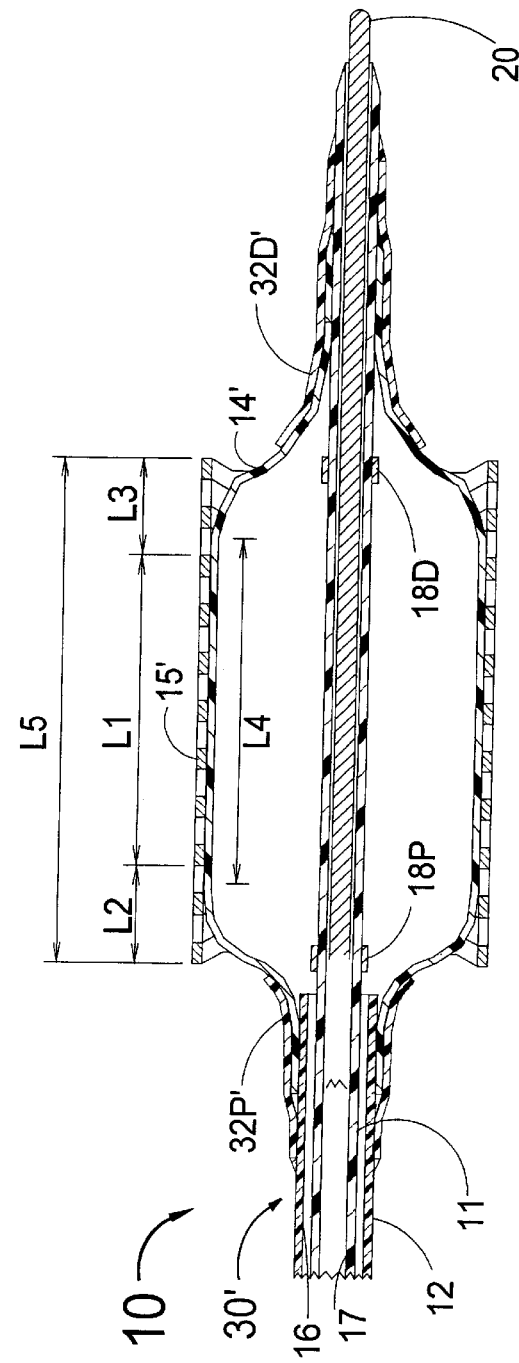
FIG. 2 is a longitudinal cross section of the system shown in FIG. 1 with the balloon inflated to deliver the stent against the wall of a stenosed vessel.

FIG. 2 is a longitudinal cross section of the distal section of the system 10' which shows the balloon 14' fully inflated which results in the stent 15' being deployed radially outward. To achieve the configuration shown in FIG. 2, the balloon 14 of FIG. 1 should be inflated to a pressure of at least 6 atmospheres and preferably to a pressure between 10 and 24 atmospheres. As the balloon 14 becomes inflated, the proximal tube 32P and the distal tube 32D each move longitudinally outward from the center of the balloon 14 thereby obtaining the shape and position of the tubes 32P' and 32D'. This provides the desired effect of uncovering the end sections of the balloon 14' so that they seek their preset state because of their shape-memory characteristic. The preset state is a cylinder having a nominal maximum diameter of the stent 15'.

As the balloon 14' becomes fully inflated, it should be noted that only the central length, L4, of the balloon 14' exerts a radially outward force to place the deployed stent 15' into a stenosis. The length L4 of the central section of the inflated balloon 14' would be measured in air at an inflation pressure of approximately 10 atmospheres. The length of the balloon expandable central section of the stent 15 (or 15') is L1. The proximal self-expanding stent section has a length L2, and the distal self-expanding end section has a length L3. The end sections L2 and L3 of the hybrid stent 15' deploy outward because that is their preset state based on their shape-memory. The preset state is set into the shape-memory of the metal of the stent 15 before it is mounted onto the balloon 14. The balloon 14' can exert a great deal of force to dilate a stenosis that would be situated within the length L4. However, the end sections L2 and L3 of the stent 15' can only exert that minimal amount of force that is generated because of the self-expanding characteristic of those end sections. This is an ideal situation from the point of view of minimizing balloon generated trauma to those portions of the vessel wall that are situated close to the edges of the deployed stent 15'. To accomplish this goal, the total length, L1+L2+L3=L5, of the stent 15' should be between 4 and 20 mm longer than the length L4 of the central portion of the balloon 14'. It should be noted that, although the lengths L2 and L3 of the end sections of the stent 15' could be different, most probably the stent 15 would be positioned onto the balloon 14' so that the length L2 is approximately equal to the length L3. It should also be noted that the length L1 of the central section of the stent 15' could be somewhat longer or somewhat shorter as compared to the length L4 of the balloon 14'.

The hybrid stent 15 could be formed from the shape-memory alloy Nitinol by having different heat treatments for the central section as compared to the end sections. The stent 15 would be heat treated to provide a transition temperature for the central section that is distinctly above 37 degrees Centigrade and the end sections would be heat treated to provide a transition temperature for the end sections that is distinctly below 37 degrees Centigrade. The stent 15 could also be formed by having a metal such as stainless steel for the central section of the stent 15 (with length L1) and welding onto that central section Nitinol end sections having lengths L2 and L3.

As is well known in the art of delivering stents into vessels of the human body, after the balloon 14' has deployed the stent 15' into the vessel, the balloon 14' is deflated and the balloon angioplasty catheter 30 and the guide wire 20 are removed from the patient's body.

It has been shown that a radioisotope stent such as described in U.S. Pat. No. 5,059,166, incorporated herein by reference can eliminate tissue growth within the stent. However, radioisotope stents have been shown to cause excessive tissue growth just beyond the edges of the stent. It is believed that this excessive tissue growth is caused by the combination of balloon trauma and radiation just beyond the edges of the radioisotope stent. Because the system 10 should eliminate balloon trauma at and beyond the edges of the deployed stent 15', it would be highly advantageous to use this system 10 for implanting a radioisotope stent. Typically one would prefer to use a beta particle emitting isotope such as phosphorous-32 to make the stent 15 radioactive. However, a gamma ray emitter such as palladium-103 is another good isotope that has been used to make stents radioactive. A gamma ray emitter is defined herein as an isotope that emits photons. Ideally, a phosphorous-32 stent should have an activity between 0.1 and 100 microCuries, and a palladium-103 stent should have an activity between 0.1 and 100 milliCuries.

Although nesting is a preferred embodiment of this invention, it should be understood that this system would perform satisfactorily if the stent were crimped onto the balloon but was not "nested". This situation is shown by the system 40 in FIG. 3. The system 40 includes a guide wire 20, a balloon angioplasty catheter 31 and a hybrid stent 35. This design uses a sheath 41 to prevent the self-expanding end sections of the stent 35 from expanding outward when the distal section of the system 40 is introduced into a vessel of a human body. After the stent 35 is placed within a stenosis in, for example, a coronary artery, the sheath 41 is pulled back in a proximal direction thereby uncovering the stent 35.

The self-expanding end sections of the stent 35 will then expand radially outward. The balloon 34 would then be promptly expanded to place the entire stent 35 in good apposition to the arterial wall. The balloon angioplasty catheter 31, guide wire 20 and sheath 41 would then be pulled out of the patient's body.

FIG. 4 represents a longitudinal cross section of one embodiment of hybrid stent of the present invention. In fact, the hybrid stent 45 of FIG. 4 would not have solid walls but would be a lace-like, thin-walled cylinder. The hybrid stent 45 has self-expanding end sections 46 and 48 and a balloon expandable central section 47. The material of the end sections 46 and 48 could be a shape-memory metal or a design in a conventional metal (such as stainless steel) that is intrinsically self-expanding. The metal and design of the central section 47 would be such that the hybrid stent 45 would not self-expand at body temperature but could be expanded by use of an inflated balloon.

FIG. 5 is a longitudinal cross section of a hybrid stent 50 in which the entire length of the stent 50 is formed from a self-expanding metal portion 51 and a balloon expandable central section 52 formed from a conventional metal that is not self-expanding. Although FIG. 5 indicates that the hybrid stent 50 is a tube with solid walls, it should be understood that a stent is in fact a lace-like, not solid-walled, thin-walled tube. For the design of FIG. 5, the end sections of the stent portion 51 would be self-expanding and the central section 52 would be balloon expandable. Typical metals for this hybrid stent 50 would be the shape-memory alloy Nitinol for the entire length of the stent 50 which includes the end sections, and a metal such as stainless steel or tantalum or a composite tube of tantalum sandwiched between outer and inner tubes of stainless steel for the balloon expandable central section 52.

FIG. 5 shows the central section 52 placed in an indentation in the self-expanding portion 51 of the stent 50. However, it should be understood that the self-expanding portion 51 could have a uniform wall thickness with the balloon expandable central section 52 being longitudinally centered and co-axially situated relative to the self-expanding portion 51. To prevent the central portion 51 from being self-expanding, the central section 52 can be co-axially mounted onto the outer surface of the portion 51. Alternatively, the central section 52 could be situated on the interior surface of the portion 51 if the portion 51 and section 52 are fixedly attached together, for example by spot welding.

An advantageous design for the hybrid stent 50 would be to have the portion 51 made from Nitinol with a transition temperature below 37 degrees Centigrade and the central section 52 being made from tantalum. An ideal wall thickness of the tantalum is approximately 0.06 mm. An ideal wall thickness for the self-expanding portion 51 is approximately the same 0.06 -mm at its central section and double that at its end sections. This stent design for the hybrid stent 50 would be ideally radio-opaque and the end sections would have a near optimum wall thickness for a self-expanding Nitinol stent. Thus this design would be ideal for placement of the central section 52 into a stenotic region of an artery, while the end sections of the portion 51 would ideally be placed in near-normal arterial sections. In this way, the edges of the stent 50 would cause minimal barotrauma to the normal arterial walls that lie just proximal and distal to the central section 52 of the stent 50. Thus the occurrence of edge dissections would be significantly decreased with this invention as compared to conventional, balloon expandable stents.

It should be understood that the metal for any balloon expandable section of a stent is defined herein as a metal that is conventional such as stainless steel or tantalum or a composite sandwich of tantalum between two tubes of stainless steel. It is of course possible to make a stent from a conventional metal such as stainless steel with the stent being self-expanding. Thus, the Wallstent® (Schneider, Plymouth Minn.) is such a self-expanding stent. To be balloon expandable and not self-expanding, the balloon expandable stent would be made from a conventional metal (i.e., without shape-memory at a temperature below body temperature) and would have a design that is not self-expanding such as the design that has been used for the Palmaz-Schatz stent. It is envisioned that the stent of the present invention could have a central section formed from a conventional, balloon expandable metal with end sections that are fabricated to be self-expanding by use of a conventional metal with a self-expanding design such as that used for the Wallstent ®.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. A system for maintaining the patency of a vessel of the human body, the system comprising:
   a flexible guide wire;
   a balloon angioplasty catheter having a lumen through which the guide wire can be slideably moved and also having a distal section where an inflatable balloon is located, the balloon having a length L4 of its cylindrical central section when the balloon is inflated to a pressure of approximately 10 atmospheres; and,
   a pre-deployed hybrid stent mounted onto the balloon of the balloon angioplasty catheter, the stent having a deployed length L5 wherein, L5>L4, the stent also having a central section that is balloon expandable and end sections that are self-expanding.

2. The system of claim 1 wherein the end sections are formed from a shape-memory alloy having a transition temperature above which it seeks its preset state, the transition temperature being below 37 degrees Centigrade.

3. The system of claim 2 wherein nitinol is used to form said end sections of the stent.

4. The system of claim 1 wherein the stent when deployed is approximately longitudinally centered on the inflated balloon.

5. The system of claim 1 wherein the length L5 is between 4 and 20 mm longer than the length L4 of the inflated balloon.

6. The system of claim 1 wherein the stent is crimped onto the balloon of the balloon angioplasty catheter.

7. The system of claim 1 wherein the stent is nested onto the inflated balloon by expanding portions of the balloon into the interstices of the non-deployed stent.

8. The system of claim 1 wherein each of the self-expanding end sections of the stent is at least partially covered by an elastomer end tube that is adapted to slide outward beyond the edges of the stent when the balloon is inflated to deploy the balloon expandable central section of the stent.

9. The system of claim 1 wherein the hybrid stent is a radioisotope hybrid stent.

10. The system of claim 9 wherein the radioisotope hybrid stent is a beta particle emitter.

11. The system of claim 10 wherein the beta particle emitter is phosphorous-32.

12. The system of claim 10 wherein the beta particle emitter has a source strength of between 0.1 and 100 microCuries.

13. The system of claim 9 wherein the radioisotope hybrid stent is a gamma ray emitter.

14. The system of claim 13 wherein the gamma ray emitter is palladium-103.

15. The system of claim 13 wherein the gamma ray emitter has a source strength between 0.1 and 100 milliCuries.

16. A method for placing a self-expanding stent within a stenosis of a vessel of a human body, the method comprising the following steps:
   a) mounting a hybrid stent having self-expanding end sections onto a balloon located at a distal section of a balloon angioplasty catheter, the self-expanding end sections being formed from a shape-memory metal having a transition temperature that is less than 37 degrees Centigrade, the stent having a length L5 that is greater than the length L4 of the cylindrical central section of the balloon when inflated to a pressure of 10 atmospheres;
   b) inserting the stent mounted onto the balloon angioplasty catheter into a stenosis within a vessel of the human body;
   c) injecting contrast medium into the balloon to a pressure of at least 6 atmospheres;
   d) deflating the balloon; and
   e) removing the balloon angioplasty catheter from the human body.

17. The method of claim 16 wherein the hybrid stent is a radioisotope hybrid stent.

18. A system for maintaining the patency of a vessel of the human body, the system comprising:
   a flexible guide wire;
   a balloon angioplasty catheter having a lumen through which the guide wire can be slideably moved and also having a distal section where an inflatable balloon is located, the balloon having a length L4 of its cylindrical central section when the balloon is inflated to a pressure of approximately 10 atmospheres; and,
   a pre-deployed, hybrid metal stent crimped onto the inflatable balloon, the stent having a deployed length L5 and also having end sections formed from a shape memory metal having a transition temperature above which it seeks its preset state which is the state when the stent has its nominal deployed diameter, the transition temperature being less than 37 degrees Centigrade.

19. The system of claim 18 wherein the metal from which the stent is made is Nitinol.

20. The system of claim 18 wherein the stent when deployed is approximately longitudinally centered on the inflated balloon.

21. The system of claim 18 wherein the length L5 is between 4 and 20 mm longer than the length L4 of the inflated balloon.

22. The system of claim 18 wherein the hybrid stent is a radioisotope hybrid stent.

23. A system for maintaining the patency of a vessel of the human body, the system comprising:
   a flexible guide wire;
   a balloon angioplasty catheter having a lumen through which the guide wire can be slideably moved and also having a distal section where an inflatable balloon is located, a pre-deployed, hybrid metal stent placed onto the inflatable balloon, the stent having end sections formed from a shape-memory metal having a transition temperature above which it seeks its preset state which is the state when the stent has its nominal deployed diameter, the transition temperature being less than 37 degrees Centigrade, the stent also having a central section that is balloon expandable at the temperature of a human body.

24. The system of claim 23 wherein the entire stent is made from Nitinol.

25. The system of claim 23 wherein the Nitinol stent has a central section that is heat treated to have a transition temperature that is distinctly above 37 degrees Centigrade and the end sections are heat treated to have a transition temperature that is distinctly below 37 degrees Centigrade.

26. The system of claim 23 wherein the stent has self-expanding end sections that are fixedly attached to a balloon expandable central section.

27. The system of claim 23 wherein the end sections are formed from Nitinol and the central section is formed from stainless steel.

28. The system of claim 23 wherein the end sections are formed from Nitinol and the central section is formed from tantalum.

29. The system of claim 23 wherein the stent when deployed is approximately longitudinally centered on the inflated balloon.

30. The system of claim 23 wherein the hybrid stent is a radioisotope hybrid stent.

31. A hybrid stent for placement within a vessel of a human body, the stent having end sections that are self-expanding and a central section that is formed from a conventional metal and has a stent design that is balloon expandable and not self-expanding.

32. The hybrid stent of claim 31 wherein the end sections are formed from a shape-memory alloy having a transition temperature that is below 37 degrees Centigrade.

33. The hybrid stent of claim 31 wherein the end sections are formed from a conventional metal in a design that is self-expanding.

34. The hybrid stent of claim 31 wherein the central section is formed from stainless steel.

35. The hybrid stent of claim 31 wherein the central section is formed from tantalum.

36. The hybrid stent of claim 31 wherein the central section is formed from a composite tube consisting of a center tube of tantalum sandwiched between two tubes of stainless steel.

37. The hybrid stent of claim 31 wherein the self-expanding end sections are made from stainless steel in a design that is self-expanding and the balloon expandable central section is made from stainless steel in a design that is balloon expandable.

38. The hybrid stent of claim 31 formed from two pieces, the first piece being a Nitinol stent that extends for the entire length of the hybrid stent and a second piece consisting of a central section formed from stainless steel that is placed within an indentation that is situated at the longitudinal center of the first portion.

39. The hybrid stent of claim 31 formed from two pieces, the first piece being a Nitinol stent that extends for the entire length of the hybrid stent and a second piece consisting of a central section formed from tantalum that is placed within an indentation that is situated at the longitudinal center of the first portion.

40. The hybrid stent of claim 31 formed from two pieces, the first piece being a Nitinol stent that extends for the entire length of the hybrid stent and a second piece which is a central section formed from a composite tube having a center tube formed from tantalum sandwiched between two tubes of stainless steel, the composite tube being placed within an indentation that is situated at the longitudinal center of the first portion.

41. A hybrid stent adapted for implantation into a vessel of a human body, the hybrid stent being formed from two pieces, the first piece being a self-expanding stent having a central section and two end sections, and a second piece being a balloon expandable stent that is shorter in length than the self-expanding stent, the self-expanding stent extending for the entire length of the hybrid stent, the second piece being co-axially placed at the center of the self-expanding stent, the balloon expandable stent being adapted to constrain expansion of the central section of the self-expanding stent.

42. The hybrid stent of claim 41 wherein the balloon expandable stent is mounted co-axially outside of the self-expanding stent.

43. The hybrid stent of claim 41 wherein the balloon expandable stent is made of stainless steel.

44. The hybrid stent of claim 41 wherein the balloon expandable stent is made of tantalum.

45. The hybrid stent of claim 41 wherein the self-expandable stent is made of stainless steel.

46. The hybrid stent of claim 41 wherein the self-expanding stent is made of Nitinol.

* * * * *